(12) United States Patent
Yang et al.

(10) Patent No.: US 8,669,085 B2
(45) Date of Patent: Mar. 11, 2014

(54) TRANSFORMATION OF GRAM POSITIVE BACTERIA BY SONOPORATION

(75) Inventors: Yunfeng Yang, Oak Ridge, TN (US); Yongchao Li, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 210 days.

(21) Appl. No.: 12/657,885

(22) Filed: Jan. 29, 2010

(65) Prior Publication Data

US 2010/0196983 A1    Aug. 5, 2010

Related U.S. Application Data

(60) Provisional application No. 61/150,097, filed on Feb. 5, 2009.

(51) Int. Cl.
*C12N 13/00* (2006.01)

(52) U.S. Cl.
USPC .................. 435/173.5; 435/173.1; 435/173.4; 435/252.7; 435/440; 435/471

(58) Field of Classification Search
None
See application file for complete search history.

(56) References Cited

U.S. PATENT DOCUMENTS 5,030,571 A  *  7/1991  Best et al. ...................... 435/227
5,656,016 A     8/1997  Ogden

FOREIGN PATENT DOCUMENTS

WO       WO 91/00358       1/1991

OTHER PUBLICATIONS

Bar, R. Ultrasound enhanced bioprocesses: Cholesterol oxidation by *Rhodococcus erythropolis*. Biotechnology and Bioengineering. 1988. 32: 655-663.*
Piyasena, P et al. Inactivation of microbes using ultrasound: a review. International Journal of Food Microbiology. 2003. 87: 207-216.*
Thompson, LA et al. Synthesis and applications of small molecule libraries. Chem. Rev. 1996. 96: 555-600.*
Boghigian, BA et al. Metabolic flux analysis and pharmaceutical production. Metabolic Engineering. 2010. 12: 81-95.*
Sojo, M et al. Cell-linked and extracellular cholesterol oxidase activities from *Rhodococcus erythropolis*. Isolation and physiological characterization. Appl. Microbiol. Biotechnol. 1997. 47: 583-589.*
Huang, W. et al. Abstract Q-164. Ultrasonic DNA transfer to gram-negative and gram-positive bacteria. in: Abstracts of the General Meeting of the American Society for Microbiology. 2008. 108: 548. Published on May 30, 2008.*
Geoghegan, M et al. The polymer physics and chemistry of microbial cell attachment and adhesion. Faraday Discussions. 2008. 139: 85-103. Published on the web on Apr. 14, 2008.*

Luchansky, JB et al. Application of electroporation for transfer of plasmid DNA to Lactobacillus, *Lactococcus, Leuconostoc, Listeria, Pediococcus, Bacillus, Staphylococcus, Enterococcus* and *Propionibacterium*. Molecular Microbiology. 1988. 2(5): 637-646.*
Phillips-Jones M.K. Chapter 23: Introduction of recombinant DNA into *Clostridium* spp. in: Nickoloff, J.A., Methods in Molecular Biology (Totowa, NJ, Humana Press Inc., 1995), vol. 47: 227-235.*
Jennert, K.C.B. Gene transfer to *Clostridium cellulolyticum* ATCC 35319. Microbiology. 2000. 146: 3071-3080.*
Liu, Y. et al., "Ultrasound: Mechanical Gene Transfer into Plant Cells by Sonoporation" *Biotechnol Adv* (2006) pp. 1-16, vol. 24(1).
Bommannan, D. et al., "Sonophoresis. II. Examination of the Mechanism(s) of Ultrasound-Enhanced Transdermal Drug Delivery" *Pharmaceutical Reasearch* (1992) pp. 1043-1047, vol. 9(8).
Lawrie, A. et al. "Ultrasound Enhances Reporter Gene Expression After Transfection of Vascular Cells In Vitro" *Circulation: Journal of American Heart Association* (1999) pp. 2617-2620, vol. 99.
Newman, C.M. et al., "Gene Therapy Progress and Prospects: Ultrasound for Gene Transfer" *Gene Therapy* (2007) pp. 465-475, vol. 14.
Joersbo, M. et al., "Direct Gene-Transfer to Plant-Protoplasts by Mild Sonication" *Plant Cell Reports* (1990) pp. 207-210, vol. 9.
Wyber, J.A. et al., "The Use of Sonication for the Efficient Delivery of Plasmid DNA into Cells" *Pharmaceutical Research* (1997) pp. 750-756, vol. 14(6).
Song, Y. et al., "Ultrasound-Mediated DNA Transfer for Bacteria" *Nucleic Acids Research* (2007) pp. 1-9, vol. 35(19).
Han, Y.W. et al., "Sonoporation is an Efficient Tool for Intracellular Fluorescent Dextran Delivery and One-Step Double-Crossover Mutant Construction in *Fusobacterium nucleatum*" *Applied and Environmental Microbiology* (2007) pp. 3677-3683, vol. 73(11).
Han, Y.W. et al. "Identification and Characterization of a Novel Adhesin Unique to Oral Fusobacteria" *Journal of Bacteriology* (2005) pp. 5330-5340, vol. 187(15).
Brenner, K. et al., "Engineering Microbial Consortia: a New Frontier in Synthetic Biology" *Trends in Biotechnology* (2008) pp. 483-489, vol. 26(9).
Mehier-Humbert, S. et al., "Plasma Membrane Poration Induced by Ultrasound Exposure: Implication for Drug Delivery" *Journal of Controlled Release* (2005) pp. 213-222, vol. 104.

(Continued)

*Primary Examiner* — Allison Ford
*Assistant Examiner* — Susan E Fernandez
(74) *Attorney, Agent, or Firm* — Scully, Scott, Murphy & Presser, P.C.

(57) ABSTRACT

The present invention provides a sonoporation-based method that can be universally applied for delivery of compounds into Gram positive bacteria. Gram positive bacteria which can be transformed by sonoporation include, for example, *Bacillus, Streptococcus, Acetobacterium,* and *Clostridium*. Compounds which can be delivered into Gram positive bacteria via sonoporation include nucleic acids (DNA or RNA), proteins, lipids, carbohydrates, viruses, small organic and inorganic molecules, and nano-particles.

12 Claims, 6 Drawing Sheets

(2 of 6 Drawing Sheet(s) Filed in Color)

(56) References Cited

OTHER PUBLICATIONS

Schlicher, R.K. et al. "Mechanism of Intracellular Delivery by Acoustic Cavitation" *Ultrasound in Medicine and Biology* (2006) pp. 915-924, vol. 32(6).

Dubey, A.K. et al., "Sequence-Specific DNA Binding by the MspI DNA Methyltransferase" *Nucleic Acids Research* (1992) pp. 3167-3173, vol. 20(12).

Tummala, S.B. et al., "Design of Antisense RNA Constructs for Downregulation of the Acetone Formation Pathway of *Clostridium acetobutylicum*" *Journal of Bacteriology* (2003) pp. 1923-1934, vol. 185(6).

Tsoi, T.V. et al., "Molecular Nature of the Pathogenic Effect Induced by *B. Cereus*" *Molecular Genetics Mikrobiol. Virusol.* (1987) pp. 18-23, vol. 7.

Jung, E.D. et al., "DNA Sequences and Expression in *Streptomyces Lividans* of an Exoglucanase Gene and an Endoglucanase Gene from *Thermomonospora Fusca*" *Applied Environmental Microbiology* (1993) pp. 3032-3043, vol. 59(9).

Tyurin, M.V. et al., "Electrotransformation of *Clostridium thermocellum*" Applied Environmental Microbiology (2004) pp. 883-890, vol. 70(2).

Fitzgerald, N.B. et al., "Sonication-Dependent Electroporation of the Erythromycin-Producing Bacterium *Saccharopolyspora erythraea*" *Applied and Environmental Microbiology* (1998) pp. 1580-1583, vol. 64(4).

Lynd, L. R., et al., "Microbial Cellulose Utilization: Fundamentals and Biotechnology", Microbiology and Molecular Biology Reviews, 66(3):506-577 (2002).

Tyurin, M. V., et al., "Role of Spontaneous Current Oscillations during High-Efficiency Electrotransformation of Thermophilic Anaerobes", Applied and Environmental Microbiology, 71(12):8069-8076 (2005).

* cited by examiner 6A    6B

TRANSFORMATION OF GRAM POSITIVE BACTERIA BY SONOPORATION

CROSS REFERENCE TO RELATED APPLICATION

This application claims the benefit of priority from U.S. Provisional Application No. 61/150,097, filed on Feb. 5, 2009.

STATEMENT REGARDING FEDERALLY SPONSORED RESEARCH OR DEVELOPMENT

This invention was made with government support under Contract Number DE-AC05-00OR22725 between the United States Department of Energy and UT-Battelle, LLC. The United States government has certain rights in this invention.

FIELD OF THE INVENTION

The present invention generally relates to transformation of Gram positive bacteria. In particular, the present invention is directed to application of sonoporation to Gram positive bacteria for delivery of a desired compound, including, but not limited to, nucleic acid molecules.

BACKGROUND OF THE INVENTION

Gene transfer is the first step of targeted genetic engineering. The commonly used DNA delivery or transformation methods can be categorized into three kinds[1]. First, certain chemicals such as calcium phosphate and DEAE-dextran are capable of permeabilizing cell membrane and facilitating DNA uptake. Although well established in several model organisms, the chemically facilitated methods suffer from very limited spectrum of applicable species. Second, liposome fusion and viral/phage infection are widely used to infect cells. This type of methods is generally efficient in DNA delivery, but it does not allow control of spatial or temporal specificity of DNA delivery. In addition, viral infection is likely to provoke the host immune response and thus prohibit gene expression and viral re-infection. Third, there are several mechanical methods including microinjection, electroporation, particle bombardment (gene gun) and sonoporation. In general, the mechanical methods are more versatile than the other two kinds, as they are less dependent on cell type. However, microinjection does require certain cell size in order to be performed under microscope; and electroporation, which permeabilizes cell membrane by high-voltage electric fields, is invasive and causes severe damage to cells. Particle bombardment couples a gene to projectiles that penetrate the membrane and hence allows for DNA delivery. However, to date this method is only amenable for surface (e.g. skin) applications. Furthermore, this and all of the aforementioned methods require repeated rounds of washing and other treatments of the cells prior to DNA transformation, making the protocol complex and difficult to be implemented in high-throughput manner.

Sonoporation has also been reported as as a DNA delivery method. Ultrasound is mechanical wave energy at frequencies above 20 kHz, which is inaudible to the human ear. The bioeffects of ultrasound include biomass heating, shear stress and mass transfer, indicating that the sonic energy could be converted into heat or mechanical energy resulting in disruption or relocation of biomass. In addition, ultrasound generates acoustic cavitation in liquid. Ultrasound generates bubbles that grow in the successive acoustic cycles. When the bubbles grow to a critical state, they suddenly collapse and release energy that can damage nearby intact cells or permeabilize cell membrane[2]. The latter phenomenon, termed reparable sonoporation, has been employed for DNA delivery since it induces temporary pores on the cell membrane for DNA uptake followed by pore resealing and cell survival.

Sonoporation as a DNA delivery method has been employed in animal cells both in vitro and in vivo. For example, 60 seconds of ultrasound exposure efficiently transfect a luciferase reporter plasmid into cultured porcine vascular smooth muscle cells (VSMCs) and endothelial cells (ECs)[3]. Furthermore, the short duration of ultrasound exposure caused only mild damage to the cell monolayer and had no impact on the plasmid integrity. More recently, there are mounting studies demonstrating sonoporation as a viable technique to transfect reporter and therapeutic gene constructs into mammalian organs in vivo[4]. However, there are few studies in non-animal species. Sonoporation is capable of DNA delivery into plant protoplast, suspension cells and intact pieces of plant tissues[5]. For the budding yeast, one study showed that a low efficiency of 2,000 transformants/microGram DNA was achieved by sonoporation[6]. For bacteria, there have been three recent studies describing sonoporation protocols for *Fusobacterium nucleatum*, *Escherichia coli*, *Pseudomonas putida* and *Pseudomonas fluorescens*[7-9], all of which are Gram negative bacteria. It remains unclear whether sonoporation is applicable to Gram positive bacteria for gene delivery.

SUMMARY OF THE INVENTION

The present invention provides a sonoporation-based method that can be universally applied for delivery of compounds into Gram positive bacteria.

The sonoporation method provided by the present invention can be applied to all groups of Gram positive bacteria, including phylum Firmicutes and Actinobacteria. In a specific embodiment, the invention provides a method for sonoporation mediated delivery of a compound into a bacteria species from a genus of phylum Firmicutes, such as, *Bacillus*, *Listeria*, *Staphylococcus*, *Enterococcus*, *Lactobacillus*, *Lactococcus*, *Leuconostoc*, *Pedicoccus*, *Streptococcus*, *Acetobacterium*, *Clostridium*, *Eubacterium*, *Heliobacterium*, *Heliospirillum*, *Megasphaera*, *Pectinatus*, *Selenomonas*, *Zymophilus*, *Sporomusa*, *Mycoplasma*, *Spiroplasma*, *Ureaplasma*, or *Erysipelothrix*. In a preferred embodiment, sonoporation-mediated delivery is directed to Gram positive bacteria selected from the group consisting of *Bacillus*, *Streptococcus*, *Acetobacterium*, and *Clostridium*.

The sonoporation approach described herein is effective for delivery of compounds to a substantially homogeneous cell population of a Gram positive bacterial species, as well as to a mixed population of cells of two or more Gram positive bacterial species. In addition, the sonoporation-mediated transformation approach of the present invention is also effective for a microbial consortium which contains one or more Gram positive bacterial species.

Compounds that can be effectively delivered into Gram positive bacteria by employing the sonoporation approach of the present invention include nucleic acids (DNA or RNA), proteins (including peptides, antigens, antibodies, etc.), lipids, carbohydrates, viruses, small molecules including organic and inorganic small molecules, molecular probes, nano-particles and biotherapeutic compounds or drugs. Generally, the compounds are not more than 75 nm in diameter, preferably, not more than 35 nm in diameter, more preferably, not more than 20 to 25 nm in diameter, or even more preferably, 15 nm or less in diameter.

According to the present invention, delivery of a desirable compound (including a nucleic acid molecule) is achieved by mixing a cell population with the compound, and subjecting the mixture to an ultrasound treatment.

Transformation efficiency may be optimized by taking into consideration, for example, the particular bacterial species and its growth status, the nature of the compound (e.g., the choice and size of the plasmid, and the nature of the selectable marker), the type of culture media (solid or liquid) subsequent to sonoporation, and the manner of the ultrasound treatment. The ultrasound treatment is applied in such a manner that effective penetration and delivery of the compound into the cells are achieved, meanwhile a sufficient number of cells remain viable. Generally speaking, the mixture of cells and compound is exposed to ultrasonic waves of a frequency range from 10 kHz to 1000 kHz, preferably from 20 to 200 kHz, more preferably 30 to 60 kHz, and most preferably about 40 kHz; with an electric energy, absorbed within the sample vial, in a range of 0.01 to 5 W/cm$^2$, or preferably 0.05 W/cm$^2$, and not more than 1 W/cm$^2$, or more preferably at least about 0.05 W/cm$^2$, and not more than to 0.5 W/cm$^2$, or even not more than 0.2 W/cm$^2$; for a period of time of up to about 5 minutes, preferably for not more than 2 minutes, more preferably not more than 1 minutes or 30 seconds. In specific embodiments, ultrasound is applied for 20 seconds, 15 second, 10 seconds or at least 5 seconds.

BRIEF DESCRIPTION OF THE DRAWINGS

This patent or application contains drawings executed in color. Copies of this patent or patent application publication with color drawings will be provided by the Office upon request and payment of the necessary fee.

DETAILED DESCRIPTION OF THE INVENTION

Figures 1A, 1B:
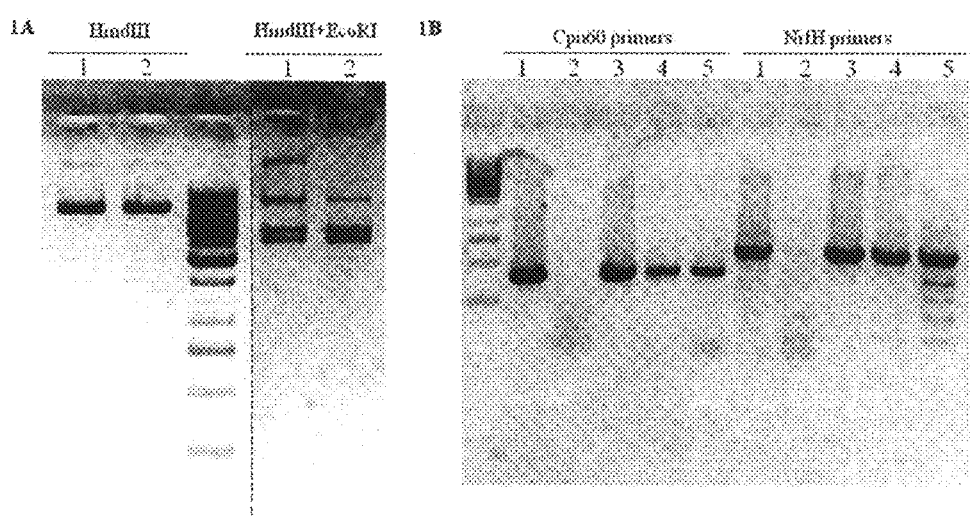
FIGS. 1A-1B. Verification of sonoporation of pSOS95Del into mesophilic *Clostridia*. (1A) Restriction enzyme digestions patterns. 1. 0.5 µg pSOS95Del used for sonoporation; and 2. 0,5 µg plasmid rescued from *E. coli* TOP10 transformed with DNA extracts of *C. phytofermentans* transformants. (1B) PCR verification of strain by strain-specific primers. 1: Wild-type *C. cellobioparum;* 2: Wild-type *C. cellulolyticum;* and 3-5: *C. cellubioparum* transformants.

The present invention is directed to application of sonoporation to Gram positive bacteria for delivery of a desired compound, including, in particular, genetic materials such as nucleic acid molecules.

It has been demonstrated for the first time, in accordance with the present invention, that Gram positive bacteria can be transformed via sonoporation. Ultrasound treatment has been shown to successfully deliver DNA plasmids into various Gram positive bacteria, including a number of *Clostridium* species of particular relevance to bioenergy applications, as well as species of *Bacillus* and *Streptomyces*. Further, in addition to delivery of nucleic acid molecules, sonoporation has also been successfully applied to introduce a chemical compound into Gram positive bacteria.

Accordingly, the present invention provides a sonoporation-based method that can be universally applied for delivery of compounds into Gram positive bacteria.

Gram positive bacteria have thick cell walls high in peptidoglycan, in contrast to Gram negative bacteria which have a negligible amount of peptidoglycan in their cell walls. Therefore, Gram positive bacteria stain dark blue or violet by Gram staining, because Gram positive bacteria are able to retian the crystal violet stain as a result of the high amount of peptidoglycan in the cell wall.

The present methods based on sonoporation can be applied to all groups of Gram positive bacteria, including phylum Firmicutes and Actinobacteria. In a specific embodiment, the present method is directed to sonoporation of a bacteria species from a genus of phylum Firmicutes, such as, for example, *Bacillus, Listeria, Staphylococcus, Enterococcus, Lactobacillus, Lactococcus, Leuconostoc, Pedicoccus, Streptococcus, Acetobacterium, Clostridium, Eubacterium, Heliobacterium, Heliospirillum, Megasphaera, Pectinatus, Selenomonas, Zymophilus, Sporomusa, Mycoplasma, Spiroplasma, Ureaplasma,* or *Erysipelothrix.*

In a preferred embodiment, the present invention provides methods for sonoporation-mediated transformation of Gram positive bacteria selected from the group consisting of *Bacillus, Streptococcus, Acetobacterium,* and *Clostridium.*

In an even more preferred embodiment, the Gram positive bacteria are *Clostridium,* including both mesophilic and thermophilic *Clostridium.*

In certain specific embodiments, sonoporation is applied to bacterial species selected from *C. phytofermentans, C. cellobioparum, C. celerecrescens, C. thermocellum, T. brockii* subsp. *Finnii, T. ethanolicus,* Caldicellulosiruptor OB47, *Anaerocellum thermophilum, Bacillus subtilis,* and *Streptococcus lividans.*

According to the present invention, the sonoporation approach described herein is not only effective for transformation of a substantially homogeneous cell population of a Gram positive bacterial species, but also effective for transformation of a mixed population of cells of two or more Gram positive bacterial species. By "substantially homogeneous", it is meant that cells of one Gram positive bacterial species constitute at least 50%, preferably at least 70%, or at least 85%, or even 95% or greated of all cells in the cell population.

Moreover, the sonoporation-mediated transformation approach provided by the present invention is also effective for a microbial consortium which contains at least one, i.e., one or more, Gram positive bacterial species. Microbial consortia, the most common life form of microbs found in the natural environments, refer to associations that microbes form with each other in close spatial proximity and synergistic or syntrophic relationships, where growth and biogeochemical cycling, and defense against potentially inhibitory environmental factors, are conducted more effectively and efficiently than on an individual population basis. It has been proposed that a microbial community can perform complicated functions that individual microbes cannot and be more robust to environmental fluctuations[10]. However, compared to single-cell microbes, a microbial community relies on communication among members within community to achieve complex functions. The methodology provided by the present invention permits transformation of Gram positive bacteria, and consequently permits genetic manipulation of microbial consortia containing at least one Gram positive bacterial species.

Examples of compounds that can be delivered to Gram positive bacteria by employing the sonoporation approach of the present invention include nucleic acids (DNA or RNA), proteins (peptides, antigens, antibodies, etc.), lipids, carbohydrates, viruses, small molecules including organic and inorganic small molecules, molecular probes such as fluorescently labeled dextran and hydrazide, nano-particles and biotherapeutic compounds or drugs. Based on current understanding of the mechanism of sonoporation[11-12], it is expected that small molecules with diameters up to 37 nm should be efficient for sonoporation mediated delivery, while molecules with diameters of more than 56 are expected to be much less efficient yet may still be transformable. Accordingly, the present method is directed to delivery of compounds that are not larger than 75 nm in diameter, preferably, not more than 35 nm in diameter, more preferably, not more than 20 to 25 nm in diameter, or even more preferably, 15 nm or less in diameter.

In a preferred embodiment, nucleic acid molecules, such as DNAs or RNAs, are introduced into Gram positive bacteria via sonoporation. A desirable genetic sequence can be placed in a plasmid vector which is introduced into Gram positive bacteria by sonoporation. The plasmid can coeveniently include additional sequences, such as an origin of replication and a selectable marker gene, that permit replication of the plasmid in the bacterial cells and selection of the transformants after sonoporation. Alternatively, nucleic acids without an origin of replicon that functions in recipient cells can also be used in accordance with the present invention, wherein the nucleic acid may be integrated into the genome of recipient cells, thereby achieving stable gene knock out/in. For transformation into certain bacterial species, such as *Clostridium cellulolyticum* and *Clostridium acetobutylicum*, it may be advantageous to protect the nucleic acid molecules by methylation (e.g., using the enzyme, MspI) prior to transformation in order to protect the molecules against degradation in the recipient bacteria. Methods of in vitro methylation of nucleic acids are well known in the art, for example, as described by Dubey (1992)[13].

In addition to nucleic acids, a variety of small molecules can be delivered into Gram positive bacteria by sonoporation. These small molecules include, but are not limited to, proteins, molecular probes (e.g. fluorescently labeled dextran and hydrazide), nano-particles and biotherapeutic compounds.

According to the present invention, delivery of a desirable compound (including a nucleic acid molecule) is achieved by mixing a cell population with the compound, and subjecting the mixture to an ultrasound treatment.

Transformation efficiency refers to the number of viable transformants obtained based on a predetermined amount of a compound to be transformed, which is often measured as colony forming units (CFU) per µg compound used. A number of factors may affect transformation efficiency, including, for example, the particular bacterial species and its growth status, the nature of the compound, the choice and size of the plasmid, the nature of the selectable marker (e.g., antibiotics), the type of culture media (solid or liquid) subsequent to sonoporation, and the manner of the ultrasound treatment.

Bacteria are generally grown to the logarithmical or early stationary phase, preferably to a cell density of at least $5 \times 10^7$ cells/ml, more preferably at least $1 \times 10^8$ cells/ml, or between $1 \times 10^8$ to $1 \times 10^9$ cells/ml. Subsequently, the cells are mixed with the compound to be delivered. In one approach, the compound is added into the bacterial culture directly without changing the culture medium or any processing or washing of the bacterial cells. Alternatively, the cells can be harvested and resuspended in defined buffers, such as PBS or HEPES. The cell-compound mixture can be kept at an appropriate temperature, including, for example, 4° C. on ice, for a period of time ranging from 0-30 minutes. Additional substances can be added to the mixture to improve transformation efficiency, for example, divalent ions such as $Ca^{++}$ and $Mg^{++}$ at a concentration in the range of 0-100 mM, commonly used surfactants (e.g. sodium lauryl sulfate), and contrast reagents including those marketed under the brand names Definity™, Optison™ and SonoVue™.

The concentration of the compound varies depending on the nature of the compound and the bacterial species to be transformed. For example, when the compound is a plasmid DNA, the plasmid can be added to the cell culture or suspension in an amout of 0.01 to 1 or 2 µg, or 10-20 µg, or even 50-100 µg, to achieve a final concentration in the range of about 5 ng/ml to about 200 µg/ml, preferably a concentration of at least 25 ng/ml, or at least 50 or 60 ng/ml, or more preferably at least 1 µg/ml.

This cell-compound mixture or suspension can be placed in a suitable container, e.g., a vial or cuvette or tube of any shape including a flat-bottom vial or an eppendorf tube, which is then placed or situated to receive ultrasonic waves. Strictly anaerobic bacteria should be handled under anaerobic condition during sonoporation.

The ultrasound treatment can be carried out by using a device capable of emitting ultrasounic waves of a desirable frequency. Preferably, the device is equipped such that the sound-emitting means within the device is supplied with electric power that is adjustable to a desirable value and the duration of the ultrasound treatment is also adjustable. The sound emiting means is formed such that the device can be immersed in a medium, e.g., a water bath, where the ultrasonic energy released from the sound-emitting means is released into the medium and transmitted to the cells inside the container which is placed also in the medium.

In order to achieve desirable transformation efficiency, the ultrasound treatment is applied in such a manner that effective penetration and delivery of the compound into the cells are achieved, and a sufficient number of cells remain viable. Generally speaking, the mixture of cells and compound is exposed to ultrasonic waves of a frequency in the range from 20 kHz to 1,000 kHz, preferably from 20 to 200 kHz, more preferably 30 to 60 kHz, and most preferably about 40 kHz or lower; with an electric energy, absorbed within the sample vial, in a range of 0.01 to 5 W/cm$^2$, or preferably 0.05 to 1 W/cm$^2$, or more preferably 0.05 to 0.2 W/cm$^2$; for a period of time of up to about 5 minutes, preferably for not more than 2 minutes, more preferably not more than 1 minutes or 30 seconds. In specific embodiments, the mixture of cells and compound is exposed to ultrasonic waves for at least 5 seconds, or for about 10 seconds, 15 seconds, or 20 seconds. The precise and preferred values for each of these parameters may vary depending upon the bacterial species, and the nature and concentration of the compound to be delivered.

After sonoporation, fresh culture medium can be added to the cell culture-compound mixture to permit the cells to recover, e.g., for one or two doubling times. Subsequently, the mixture can be plated onto solid media for selection of transformants, or further expanded in liquid culture media containing a substance (e.g., antibiotics) appropriate for selection and enrichment of transformants. For thermophiles, it may be preferable to culture the cells in semi-solid media after sonoporation, as the plating efficiency on solid media may be low.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are considered to be included within the scope of the invention. All the publications mentioned in the present disclosure are incorporated herein by reference.

EXAMPLES

Example 1

Establishing Low Frequency Sonoporation in Mesophilic *Clostridia*

Sonoporation using low frequency 40 kHz ultrasound was tested in three mesophilic *Clostridia*: *C. phytofermentans*, *C. celerecrescens* and *C. cellobioparum*. These bacteria have a potential for use in consolidated bioprocessing (CBP), which combines cellulose hydrolysis and fermentation in a single process, but had not been transformable prior to this study. All of the *Clostridia* strains were grown in CSM2 medium having the following composition: 0.5 g NaHCO$_3$, 0.25 g Na$_2$S*9H$_2$O, 10 mg FeSO$_4$*6H$_2$O, 1 g Cysteine HCl, 2.75 g base MOPS, 1 g K$_2$HPO$_4$, 1.3 g (NH4)$_2$SO$_4$, 0.5 g KH$_2$PO$_4$, 0.5 g MgCl$_2$*6H$_2$O, 0.1 g CaCl$_2$*2H$_2$O, 5 g Cellobiose, 5 g Yeast Extract, 1000×ATCC Vitamins, and 1000×ATCC Minerals, dissolved in water to 1 L.

0.5 ml cell cultures grown to late log phase (having a cell density of 10$^8$-10$^9$ cells/ml) were mixed with 0.5 µg plasmid pSOS95Del, a plasmid described by Tummala (2003)[14], in flat-bottom glass vials. The vials were immersed in a standard 40 kHz ultrasonic cleaner Branson 200 apparatus (having an overall size of 8.7"×4.5"×5", and a tank size of 6.5"×3.5"×2.2", available from Branson Ultrasonics Corp., Danbury, Conn.), which contained 0.2 liter of MiliQ water, and ultrasound treatment was applied for 5-10 seconds. Afterwards, 0.5 ml fresh growth medium was added to the vials and the vials were kept at 34° C. for about one doubling time before plating onto solid media containing 10 µg/ml erythromycin. The plates were incubated in a glove bag maintained at 34° C. The success of transformation was evident based on appearance of colonies on the solid media after 3-7 days. In control samples treated with sonoporation in the absence of the plasmid DNA, no colonies of spontaneous mutants exhibiting resistance to erythromycin were observed. In other control samples treated with the plasmid in the absence of ultrasound, no colonies were observed, indicating that ultrasound was critical for transformation. The transformation efficiency is shown in Table 1.

To verify the existence of pSOS95Del in the transformants, three ultrasound-transformants of each species were randomly picked for DNA extraction. Direct visualization of plasmid was not evident when DNA was separated by electrophoresis. However, PCR performed using two sets of primers specific to pSOS95Del revealed bands of expected sizes, which suggested the presence of plasmid DNA in the transformants. Therefore, plasmid rescue experiments were carried out in which extracted DNA was used to transform *E. coli* TOP10. Plasmid DNA was repeatedly recovered from *E. coli* transformants. The similarity of the restriction enzyme digestion patterns for pSOS95Del used for sonoporation and recovered from *E. coli* transformants indicated that no DNA rearrangement occurred (FIG. 1A). In addition, the plasmids were sequenced to confirm their identity.

The identity of the transformants of each species was verified by 16S rDNA sequencing of each colony used in plasmid verification. Indeed, the transformants had 16S rDNA sequences identical with those of *C. phytofermentans*, *C. celerecrescens* or *C. cellobioparum*. The strain identity was also confirmed by PCR with strain-specific primers using DNA prepared from individual clones of transformants. For example, a set of *C. cellobioparum*—specific primers was able to generate PCR band for wild-type (WT) and transformed *C. cellobioparum*, but not a related species *C. cellulyticum* (FIG. 1B).

Example 2

Figure 2A:
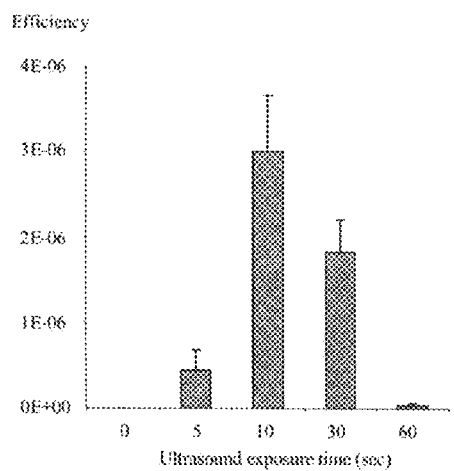
FIGS. 2A-2C. Effects on sonoporation efficiency of *C. phytofermentans*. (A) Ultrasound treatment for 5-60 seconds delivered pSOS95Del to *C. phytofermentans*. Exposure time of 10 seconds yielded the highest efficiency. (B) The effect of plasmid concentration on transformation of *C. phytofermentans*. (C) The effect of physiological status of bacteria on transformation of *C. phytofermentans*. 1-4 are four sampling points for sonoporation representative of early-, mid- and late-logarithmic phase and stationary phase, respectively.
Figure 2B:
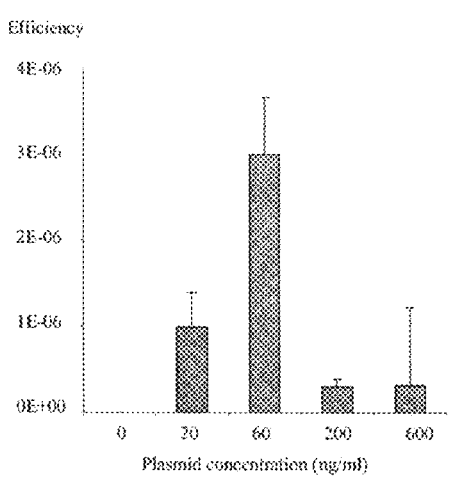
Figure 2C:
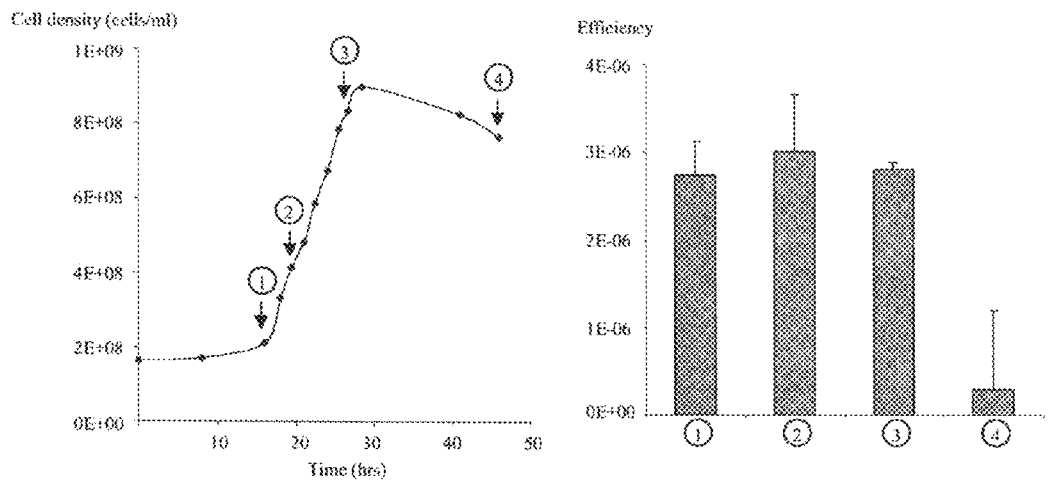

The Effects of Duration of Sonoporation, Plasmid Concentration and Cell Density or Growth Status on Transformation Efficiency Experiments were carried out in *C. phytofermentans* to evaluate factors that influence transformation efficiency. DNA transformation has the highest efficiency of ~2,000 CFU/µg DNA when exposed to ultrasound for 10 seconds (FIG. 2A) and at plasmid concentration of 60 ng/ml (FIG. 2B). Extended ultrasound exposure to 60 seconds significantly reduced the efficiency. This observation is consistent with a similar study in the gram negative bacterium *Pseudomonas putida* (Song, 2007)[7], which suggested that prolonged ultrasound treatment could damage both plasmid and bacterial cells and thus impair transformation efficiency. In addition, the physiological status of bacteria host impacted DNA transformation, as the efficiencies were high when the bacterial population underwent exponential growth, but dropped dramatically after cells entered stationary phase (FIG. 2C). This is likely due to the rigid structure and composition of gram-positive cell wall during stationary phase[11], which could impair ultrasound permeabilization for DNA uptake.

Example 3

Establishing Sonoporation in Thermophilic Bacteria

Thermophilic bacteria of bioenergy relevance, including *Clostridium thermocellum*, *Anaerocellum thermophilum* and a novel environmental isolate from Yellow Stone National Park Caldicellulosiruptor OB47, were subjected to sonoporation. Plasmid pHV33 (Tsoi et al, 1987)[15] carrying a thermostable cat gene that confers resistance to chloramphenicol was used in these experiments.

Figures 3A, 3B:
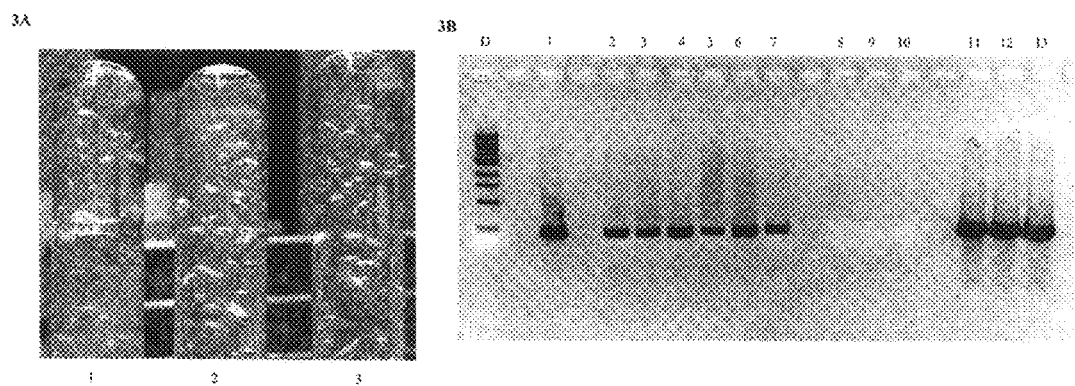
FIGS. 3A-3B. (3A) Colony formation of thermophilic CBP bacteria in a solid medium. Air bubbles were formed by trapping of $CO_2$ and $H_2$ produced during bacterial growth. (3B) PCR verification of plasmid transformation by primers specific for pHV33. Lane 1-12 used DNA templates prepared from individual clones of transformants of *C. thermocellum, A. thermophilum* and OBP47, respectively. Lane C was a positive control using pHV33 as DNA template of PCR reaction.

A similar protocol to Example 1 was applied. In brief, cells were grown to late logarithmic phase. 0.2 ml cell cultures were mixed with 1.5 µg plasmid in flat-bottom glass vials. The vials were immersed in a standard 40 kHz ultrasonic cleaner Branson 200 apparatus, which contained 0.2 liter of MiliQ water, and ultrasound treatment was applied for 10 seconds. Afterwards, 0.2 ml cell cultures with plasmids were injected into anaerobic culture tubes containing 10 ml growth medium and were kept at 60° C. for about one doubling time before chloramphenicol and Gelrite agar were injected into the tubes to the final concentration of 75 µg/ml and 0.6%, respectively. The plates were incubated at 60° C. Single colonies appeared in semi-solid media after 3-7 days (FIG. 3A). All of the protocols were conducted under anaerobic condition.

16S rDNA sequencing using three pure cultures of transformants for each species confirmed their identities. To verify the presence of pHV33, PCR performed using two sets of primers specific to pHV33 revealed bands of expected sizes, which suggested the presence of plasmid DNA in the transformants (FIG. 3B). Plasmid rescue experiments from *E. coli* were carried out as described in the previous section. The plasmids isolated from *E. coli* TOP10 were digested with HindIII and compared to pHV33, which showed plasmid rearrangement. The rearrangement of plasmids was further confirmed by sequencing.

Example 4

Establishing Sonoporation in *Bacillus* and *Streptomyces* Species

Figure 4:
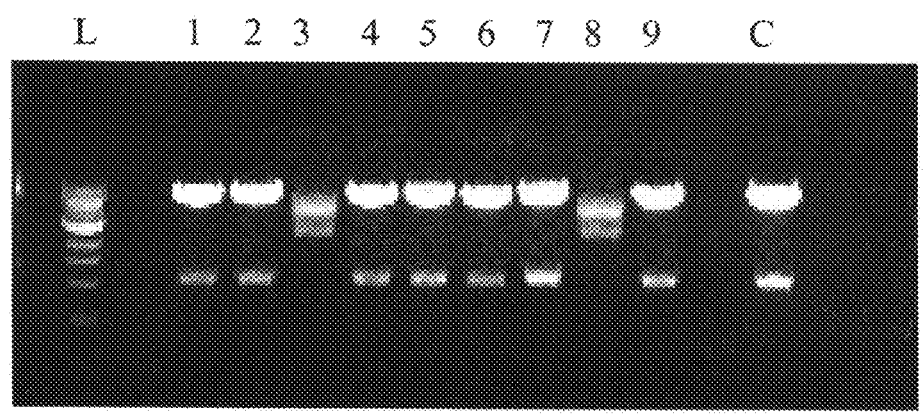
FIG. 4. Verification of sonoporation of pSES1 into *S. lividans* by NcoI-digestion of plasmid DNA. Lane 1-9: plasmid isolated from 9 individual clones of transformed *S. lividans*; L: DNA ladder; and C: pSES1 as positive control.

*Bacillus subtilis* cells were grown in LB medium to mid-logarithmiuc phase. 0.5 ml cell culture was mixed with 1.0 µg plasmid pUB110 in flat-bottom glass vials and ultrasound treatment was applied (40 kHz, 10 seconds). Afterwards, the mixture was transferred into a 1.5 ml eppendorf tube and 0.5 ml LB medium was added into the culture. The tube was kept at 37° C. for two hours and then the cells were spread on a LB plate with 20 µg/ml kanamycin and incubated at 37° C. Single colonies appeared after 24 hours. Plasmids were extracted from the transformants directly, cut by BamHI/NcoI, and compared with pUB110. Identical enzyme digestion pattern was observed. The identity of the transformants of each species was verified by 16S rDNA sequencing. *Streptomyces lividans* cells were grown in TSB medium[16] at 30° C. in shake flasks containing stainless steel springs for 2-4 days until high cell density was reached. The cells were collected by centrifugation and were responded in PBS buffer plus 10.3% sucrose. 0.2 ml cells were mix with 4.0 µg non-methylated pSES1 plasmids in flat-bottom glass vials and ultrasound treatment was applied (40 kHz, 10 seconds). Afterwards, the cell culture with plasmids was transferred into a 1.5 ml eppendorf tube and 0.5 ml TSB medium was added into the culture. The tube was kept at 30° C. for 2 hours and then the cells were spread on a TSB plate, overlaid with 8 ml LB nutrient soft agar containing 25 µg/ml thiostrepton and incubated at 30° C. Colonies appeared on the plate after 3-5 days. pSES1 could not be visualized on the gel directly when prepared directly from the transformants. However, PCR performed using one set of primers specific to pSES1 revealed bands of expected sizes, which suggested the presence of plasmid DNA in the transformants. Plasmid rescue experiments were carried out in which extracted DNA was used to transform *E. coli* TOP10. The plasmids isolated from *E. coli* TOP10 were digested with NcoI and compared to wild-type pSES1. The majority of the plasmids showed identical enzyme digestion pattern to wild-type pSES1 (FIG. 4). The identity of the transformants of each species was verified by 16S rDNA sequencing.

Example 5

Figure 5:
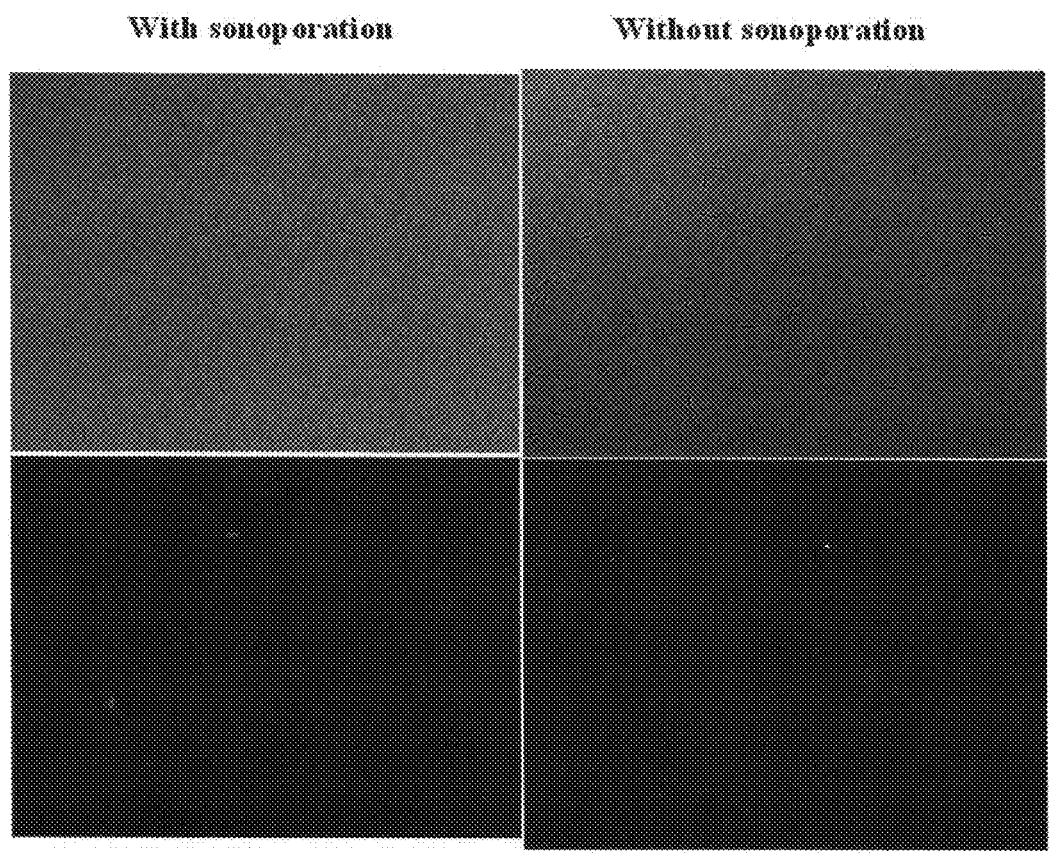
FIG. 5. Microscopic examination of DNA uptake, as labeled with FITC, by *C. phytofermentans* with or without sonoporation.

Microscopic Examination of DNA Uptake in *C. Phytofermentans* pSOS95Del was covalently labeled with FITC, mixed with *C. phytofermentans* cultures and the effect of sonoporation was examined by fluorescence microscopy. Strong staining of bacterial cells was visualized after ultrasound treatment for 20 seconds (FIG. 5). In the absence of ultrasound treatment, only low level of background fluorescence was present.

Example 6

Figure 6A:
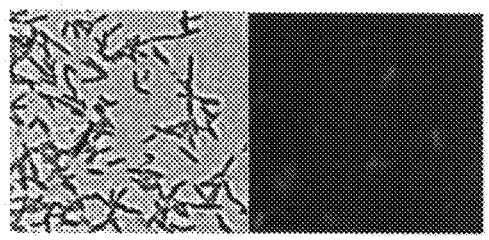
FIGS. 6A-6B. Delivery of Texas Red-conjugated dextran into *C. thermocellum* by sonoporation, as shown by fluorescent dextran uptake by *C. thermocellum* with (6A) and without (6B) ultrasound treatment, respectively.
Figure 6B:
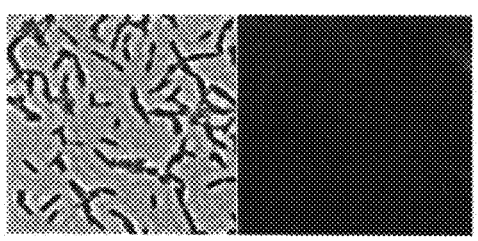

Introduction of Texas Red-Conjugated Dextran into *C. Phytofermentans* by Sonoporation 0.2 ml *C. phytofermentans* cells were mixed with 40 µl 2.5 mg/ml Texas Red-conjugated dextran (70 kDa; Invitrogen) and subjected to sonoporation treatment for 2 minutes. Then the mixture was transferred to microcentrifuge tubes, washed four times in 500 µl phosphate-buffered saline (PBS), each followed by centrifugation at 14 krpm, and resuspended in 500 µl PBS. The bacterial cells were then examined under a fluorescence microscope. A control experiment omitting the sonoporation step was included in parallel for comparison. The sample treated with sonoporation showed strong fluorescence signal for a large percentage of bacterial cells (FIG. 6). The control sample showed some background, albeit weaker, signals in some cells.

TABLE 1

Summary of transformation efficiency of a diversity of Gram positive bacteria by sonoporation.

| Strain | Efficiency (CFU/µg DNA) |
|---|---|
| C. phytofermentans | 2,000 +/− 300 |
| C. celerecrescens | 280 +/− 60 |
| C. cellobioparum | 170 +/− 55 |
| A. thermophilum | 275 +/− 100 |
| OBP47 | 206 +/− 63 |
| B. subtilis | 10-100 |
| S. lividans | <1 |

REFERENCES

1. Liu, Y., Yang, H. & Sakanishi, A. Ultrasound: mechanical gene transfer into plant cells by sonoporation. *Biotechnol Adv* 24, 1-16 (2006).
2. Bommannan, D., Menon, G. K., Okuyama, H., Elias, P. M. & Guy, R. H. Sonophoresis. II. Examination of the mechanism(s) of ultrasound-enhanced transdermal drug delivery. *Pharm Res* 9, 1043-1047 (1992).
3. Lawrie, A. et al. Ultrasound enhances reporter gene expression after transfection of vascular cells in vitro. *Circulation* 99, 2617-2620 (1999).
4. Newman, C. M. & Bettinger, T. Gene therapy progress and prospects: ultrasound for gene transfer. *Gene Ther* 14, 465-475 (2007).

5. Joersbo, M. & Brunstedt, J. Direct Gene-Transfer to Plant-Protoplasts by Mild Sonication. *Plant Cell Rep* 9, 207-210 (1990).
6. Wyber, J. A., Andrews, J. & D'Emanuele, A. The use of sonication for the efficient delivery of plasmid DNA into cells. *Pharm Res* 14, 750-756 (1997).
7. Song, Y. et al. Ultrasound-mediated DNA transfer for bacteria. *Nucleic Acids Res* (2007).
8. Han, Y. W., Ikegami, A., Chung, P., Zhang, L. & Deng, C. X. Sonoporation is an efficient tool for intracellular fluorescent dextran delivery and one-step double-crossover mutant construction in *Fusobacterium nucleatum*. *Appl Environ Microbiol* 73, 3677-3683 (2007).
9. Han, Y. W. et al. Identification and characterization of a novel adhesin unique to oral fusobacteria. *J Bacteriol* 187, 5330-5340 (2005).
10. Brenner, K., You, L. & Arnold, F. H., Engineering microbial consortia: a new frontier in synthetic biology. *Trends Biotechnol* 26, 483-489 (2008).
11. Mehier-Humbert, S., Bettinger, T., Yan, F. & Guy, R. H. Plasma membrane poration induced by ultrasound exposure: implication for drug delivery. *J Control Release* 104, 213-222 (2005).
12. Schlicher, R. K. et al. Mechanism of intracellular delivery by acoustic cavitation. *Ultrasound Med Biol* 32, 915-924 (2006).
13. Dubey, A. K. & Roberts, R. J. Sequence-specific DNA binding by the MspI DNA methyltransferase. *Nucleic Acids Res* 20, 3167-3173 (1992).
14. Tummala, S. B., Welker, N. E. & Papoutsakis, E. T. Design of antisense RNA constructs for downregulation of the acetone formation pathway of *Clostridium acetobutylicum*. *J Bacteriol* 185, 1923-1934 (2003).
15. Tsoi et al., *Mol. Gen. Mikrobiol. Virusol.* 18-23 (1987).
16. Jung E D, Lao G, Irwin D, Barr B K, Benjamin A, Wilson D B. "DNA sequences and expression in *Streptomyces lividans* of an exoglucanase gene and an endoglucanase gene from *Thermomonospora fusca*." *Appl Environ Microbiol.* 1993 September; 59(9):3032-43.

What is claimed is:

1. A method of delivering a compound into bacteria comprising a *Clostridium* species, comprising mixing said bacteria with said compound, and subjecting the mixture to ultrasound treatment, wherein said ultrasound treatment delivers said compound into the interior of the bacterial cell.

2. The method of claim 1, wherein said ultrasound treatment is characterized by providing ultrasonic waves of a frequency in the range of 20 to 80 kHz, having an electric power output in the range of at least 0.01 to 5 $W/cm^2$, for a period of time of not more than 2 minutes.

3. The method of claim 2, wherein said frequency is about 40 kHz or lower.

4. The method of claim 2, wherein said electric power output is not more than 1 $W/cm^2$.

5. The method of claim 2, wherein said ultrasonic waves are provided for not more than 15 seconds.

6. The method of claim 1, wherein said compound is selected from the group consisting of a nucleic acid, protein, lipid, carbohydrate, virus, an organic or inorganic molecule with a diameter of not larger than 75 nm in diameter, and a nano-particle.

7. The method of claim 6, wherein said compound is a nucleic acid.

8. The method of claim 7, wherein the concentration of said nucleic acid in said mixture is about 25 ng/ml.

9. The method of claim 1, wherein said bacteria is a microbial consortium comprising at least one *Clostridium* species.

10. The method of claim 1, wherein said bacteria have been cultured to the late log phase or the early stationary phase prior to mixing with said compound.

11. The method of claim 10, wherein said bacteria have been grown to a cell density of at least $1 \times 10^8$ cells/ml prior to mixing with said compound.

12. The method of claim 10, wherein said mixing is done by adding said compound directly into the culture of said bacteria in a culture medium prior to said ultrasound treatment.

* * * * *